United States Patent [19]

Cattran et al.

[11] 4,252,537

[45] Feb. 24, 1981

[54] QUANTIFICATION OF THE MUNITIONS, HMX, RDX, AND TNT IN WASTE WATER BY LIQUID CHROMATOGRAPHY

[75] Inventors: Doris E. Cattran; Thomas B. Stanford, both of Columbus; Anthony P. Graffeo, Worthington, all of Ohio

[73] Assignee: The United States of America as represented by the Secretary of the Army, Washington, D.C.

[21] Appl. No.: 8,723

[22] Filed: Feb. 2, 1979

[51] Int. Cl.³ .............................................. B01D 15/08
[52] U.S. Cl. .................................. 23/230 R; 210/656
[58] Field of Search .................. 210/31 C, 198 C; 23/230 R, 230 M

[56] References Cited

U.S. PATENT DOCUMENTS

| | | | |
|---|---|---|---|
| 3,884,802 | 5/1975 | Spaans | 210/31 C |
| 4,108,604 | 8/1978 | Heller | 23/230 R |
| 4,157,299 | 6/1979 | Landownr | 210/31 C |

OTHER PUBLICATIONS

The Determination of Selected Munitions and Their Degradation Products Using High Performance Liquid Chromatography by Meier et al., Published by the American Chemical Society from 4th Joint Conference of Sensing of Envioronmental Pollutants, Published Mar. 1, 1978, Conference Nov. 6–11, 1977.

Introduction to Modern Liquid Chromatography by Snyder and Kirkland, John Wiley and sons, N.Y., N.Y., pp. 142–144, 200-203, 227–229, 469 and 198.

Thin Layer Chromatography an Annotated Bibliography, 1964–1968, pp. 142–145, by Haywood, Ann Arbor Science Publishers, Ann Arbor, Mich., 1968.

*Primary Examiner*—John Adee
*Attorney, Agent, or Firm*—William G. Gapcynski; Werten F. W. Bellamy; Arthur I. Spechler

[57] ABSTRACT

Disclosed is a liquid chromatography process for the quantitative determination of nitro-amines and nitro-aromatics in liquid samples, which comprises directly injecting a liquid sample containing these compounds onto a liquid chromatography column, separating the compounds on the column by elution, and then monitoring the ultra-violet absorbance of the resulting eluant. The instant process finds particular application in the quantitative detection of munitions, such as HMX, RDX, TNT, and their degradation products, in aqueous effluent streams.

6 Claims, 6 Drawing Figures

QUANTIFICATION OF THE MUNITIONS, HMX, RDX, AND TNT IN WASTE WATER BY LIQUID CHROMATOGRAPHY

BACKGROUND OF THE INVENTION

The present invention relates to a process for the quantitative detection of aliphatic nitroamines and nitroaromatics in liquid samples. It particularly relates to a liquid chromatography method for the quantitative determination of aliphatic nitroamines and nitrated aromatics in liquid samples, such as waste water samples.

The development of a rapid and quantitative method for the determination of trace quantities of aliphatic nitro-amines and nitroaromatics in aqueous effluent streams has recently become necessary as a result of an increasing concern for the presence and fate of munitions-related materials in the environment. Compounds of such as 1,3,5,7-tetranitro-1,3,5,7-tetraazacyclooctane (HMX), 1,3,5-trinitro-1,3,5-triazacyclohexane (RDX), and 2,4,6-trinitrotoluene (TNT) are typical members of these classes of explosive materials, and represent a significant portion of the munitions currently being produced in the United States. The occurrence of these and related materials in the environment is primarily a result of the discharge of aqueous process streams utilized during the synthesis of these compounds into the environment.

Heretofore, the prior art has developed many methods for the compositional analysis and for the determination of the purity of explosive mixtures. Typical examples of these prior art analysis methods include infrared spectroscopy, thin layer chromatography, and liquid chromatography. While these methods have proven adequate in the compositional analysis of nitrated explosives, the low sensitivities thereof preclude the use of such methods in the detection of trace quantities of these compounds, such as are involved in environmental analysis. Due to its much higher sensitivity, gas chromatography has therefore been used almost exclusively for the determination of trace levels of explosives. However, the gas chromatography analysis method is only suitable for use with those nitro-compounds which are relatively volatile at the temperatures employed therein. Since many aliphatic nitro-amines, nitroaromatics, and other nitrated compounds are non-volatile at these temperatures, gas chromatography is suitable for the detection of only a limited portion of these compounds. This inability to analyze many of the nitro munitions thus renders gas chromatography unsuitable for use in environmental analysis.

Moreover, it is an objective of any analysis procedure to limit sample losses to a minimum in order to insure accuracy of measurement. One of the principal sources of sample loss is due to the sample manipulation required in the analysis procedure. Due to the extensive sample manipulation necessary in gas chromatography, significant amounts of the nitrated compounds present in the sample are lost to thermal and photolytic degradation. Consequently, not only is the applicability of gas chromatography limited to a small group of compounds, but the results obtained thereby have a low and undesirable accuracy. Additionally, in order to maximize accuracy it is desirable that the chosen method of analysis should have the ability to detect any degradation products resulting from decomposition of the sample. With gas chromatography, as has been aforementioned, the ability to detect such degradation products is limited to those which are volatile at the temperatures employed therein.

Accordingly, in view of the large importance of nitrated compounds, and particularly the nitrated explosives TNT, RDX, and HMX, and the large concern for the existence of these compounds in the environment, there exists a great need in the art for a rapid and accurate method for quantitatively detecting trace quantities of these contaminants in liquid samples.

SUMMARY OF THE INVENTION

Accordingly, it is an object of the present invention to provide a method for quantitatively detecting the presence of nitro-amines and nitroaromatics in liquid samples.

It is a particular object of the present invention to provide a quantitative method for the analysis of nitro-amines and nitroaromatics in liquid samples, which has a sensitivity sufficient to enable trace quantities of these compounds to be detected.

It is a further object of the present invention to provide a quantitative analysis method for nitro-amines and nitroaromatics which minimizes sample handling, sample losses, and is suitable for use with both volatile and non-volatile compounds of these types.

It is a specific object of the present invention to provide a rapid and highly accurate method for the quantitative detection of trace quantities of nitrated explosives, such as HMX, RDX, and TNT in aqueous waste water.

In accomplishing the foregoing and other objects, there has been provided in accordance with the present invention a method for the quantitative detection of aliphatic nitro-amines and nitroaromatics in liquid samples which minimizes the problems of low volatility and thermal instability commonly associated with the sample preparation and analysis of these compounds. The method of the instant invention comprises a rapid and highly efficient liquid chromatography analysis method for the quantitative detection of nitro-amines, nitroaromatics, and other nitrated compounds in liquid samples, comprising the steps of directly injecting a liquid sample containing these compounds onto a high performance liquid chromatographic column; chromatographically separating the compounds on the column by elution with a suitable mobile phase, and then monitoring the absorbance of the resulting eluant in the ultraviolet region to provide a quantitative determination of each of the nitrated compounds present in the sample. By directly injecting the liquid sample onto the high performance liquid chromatographic column, the thermal and photolytic instability attendant extensive sample handling is minimized. Moreover, the high performance liquid chromatographic separation method of the instant invention is applicable to both high and low volatility compounds, and the large sample volumes which can be injected in this type of chromatography enables trace quantities of these compounds, such as, for example, the quantities in which these compounds are present in the environment, to be accurately and quantitatively detected. Accordingly, the process of the instant invention provides a highly suitable quantitative analysis method for nitro-amines, nitroaromatics, and other nitrated compounds.

Broadly, the analysis method of the instant invention is highly suitable for use with any of the nitro group containing compounds well known to those skilled in the art which have an absorbance in the ultra-violet region of the light spectrum. The only limitation on the types of compounds which can be analyzed and detected by the instant analysis method is that these compounds must exhibit an absorbance in the ultra-violet region. Examples of compounds well known in the art to exhibit an absorbance in this region include the nitroamines and the nitroaromatics, and the analysis method of the instant invention is highly suitable for use in detecting the compounds of each of these classes. Within each of these classes of compounds, the quantitative analysis method of the instant invention is particularly advantageous for use in the detection and determination of trace quantities of the nitro-amine and nitroaromatic explosives, typical examples of which include 1,3,5,7-tetranitro-1,3,5,7-tetraazacyclooctane (hereinafter referred to as HMX), 1,3,5-trinitro-1,3,5-triazacyclohexane (hereinafter referred to as RDX) and 2,4,6-trinitrotoluene (hereinafter referred to as TNT), in the environment, since a satisfactory method for the environmental analysis of these compounds has heretofore been lacking in the prior art.

Other objects, features, and advantages of the instant invention will become apparent to the skilled artisan upon examination of the following detailed description of the present invention, taken in conjunction with the figures of drawing, wherein:

DETAILED DESCRIPTION OF THE PREFERRED EMBODIMENTS

Figure 1:
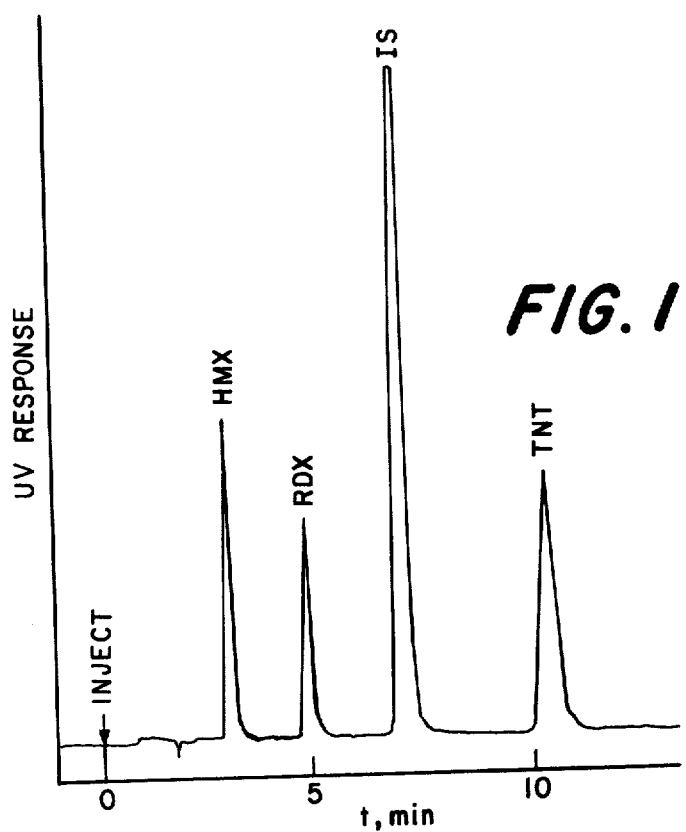
FIG. 1 is a chromatogram resulting from the analysis of a 100 microliter sample of a standard solution containing 10 ppm each of HMX, RDX, and TNT by the analysis method of the instant invention.

In contrast to gas chromatography, the analysis method of the instant invention is highly suitable for use in the detection of both non-volatile and volatile nitrated compounds. Moreover, the sensitivity of the instant analysis method is such that amounts of these compounds ranging over very wide levels may be readily and accurately determined, including trace quantities of these compounds. With the prior art methods of analysis wherein only very small sample sizes can be accommodated, detection of trace quantities of the nitro compounds can be achieved only by first concentrating the sample to a volume which can be utilized by the analysis method. As a direct consequence of this necessity for concentrating the sample, significant amounts of the nitrated compounds are lost to thermal and photolytic degradation. As a result, the sensitivity and accuracy of these prior art methods of analysis is very low, rendering these methods unsuitable for use in the direction of trace quantities of these compounds, such as, for example, are involved in environmental analysis. In accordance with the inventive concepts of the instant invention, however, applicants have found that the aforementioned deficiencies of the prior art may be obviated through the use of a high performance liquid chromatographic analysis method wherein the sample is directly injected onto the chromatographic column. By directly injecting the sample onto the liquid chromatography column, the problems which have heretofore been associated with the sample preparation and analysis of the nitrated compounds are minimized. Moreover, in contrast to the prior art methods, high performance liquid chromatography can accommodate samples of sufficient volume size that trace quantities, as low as a few parts per billion, can readily be detected without the necessity for concentration of the sample or other sample preparation steps. In contradistinction to the prior art, therefore, the present analysis method minimizes sample handling, accruing thereby substantial improvement in analysis sensitivity and accuracy.

As has been aforementioned, the method of the instant invention is highly suitable for use with any of the nitrated compounds well known to those skilled in the art which exhibit an absorbance in the ultraviolet range. Moreover, the process of the instant invention is uniquely suited for the quantitative detection of the nitro-amine and nitroaromatic explosives and their degradation products in waste water and other liquid samples, wherein these compounds are present in trace quantities, for example, quantities in the parts-per-billion and parts-per-million range, since a satisfactory method for the analysis of these types of compounds in such quantities has heretofore been lacking in the prior art. Any of the explosives of each of these classes, or other nitrated compounds well known to those skilled in the art having an absorbance in this range may be successfully analyzed by the method of the instant invention. By way of illustration, but not of limitation, typical examples of these types of compounds include nitrated phenols, such as meta-nitro phenol, HMX, RDX, TNT, para-amino dinitrotoluene, trinitrobenzene, dinitro-benzene, 2,5-dinitrotoluene, 2,6-dinitrotoluene, 2,4-dinitrotoluene, 3,4-dinitrotoluene, 3,5-dinitrotoluene, 2,3-dinitrotoluene, and other similarly nitrated compounds well known to those skilled in the art. In view of their extensive use, the difficulty in analysis, and the large concern for their fate in the environment, the nitro-amine and nitroaromatic explosives HMX, RDX, TNT, and their degradation products are particularly suitable candidates for analysis by the present invention, although it is to be emphasized that any compound carrying a nitro-group is suitable for detection by the instant method.

A futher requirement of the instant invention is that the sample to be tested be directly injected and then separated on a high performance liquid chromatographic column in order to reduce sample losses to a minimum and thereby enhance the accuracy of the analysis. As has been discussed supra, high performance liquid chromatography is particularly suitable for this purpose since in this method of chromatography the liquid sample can be injected directly onto the column. Moreover, relatively large sample volumes can be accommodated in this type of chromatography. This advantage accrues a greatly increased sensitivity to very small quantities of the nitrated compounds, and completely eliminates the necessity for concentration steps and other sample preparation steps which have heretofore been necessary for the detection of small quantities of these compounds, and the substantial losses resulting therefrom. In fact, applicants have found that the analysis method of the instant invention may be successfully utilized to detect quantities of nitro compounds as low as about 25 parts per billion, and can accommodate sample volumes of up to about 400 microliters with satisfactory accuracy and reproducibility.

As is well known to those skilled in the art, in high performance liquid chromatography, a mobile phase into which the sample has been directly injected is pumped at high pressures, for example up to about 300 atmospheres at flow rates from about 0.2 to 10 milliliters per minute through packed columns. The eluant exiting from the column is then monitored with a suitable detection system, which in the instant invention comprises an ultra-violet detector, to provide a quantitative determination of each compound present in the sample. Apparatus for this type of chromatography generally will include a high performance liquid chromatographic column, a high pressure pump, a suitable injection apparatus, an ultra-violet detector, and optionally, suitable integration equipment for quantifying the results. A typical high performance liquid chromatographic system is described in U.S. Pat. No. 3,884,802, the entirety of which is herein incorporated by reference. When greater efficiency in separation is required, a plurality of the high performance liquid chromatographic columns connected in series may also be utilized.

Any high performance liquid chromatographic apparatus well known to those skilled in the art is suitable for use in the instant invention. The only requirement of the instant invention is this regard is that the apparatus utilize a high performance liquid chromatographic columns. This type of column is well known to those skilled in the art and is commercially available. Due to its high efficiency, particularly preferred for use in the instant invention is the reverse-phase, high performance liquid chromatographic column marketed by Waters Associates of Milford, Massachusetts under the trade designation $\mu$ Bondapak $C_{18}$. This type of high performance liquid chromatographic column comprises a pre-packed column having a monomolecular layer of octadecyltrichlorosilane chemically bonded to porous silica beads having an average particle size of about 10 microns.

As has been aforementioned, in high performance liquid chromatography, a mobile phase is pumped under pressure through the liquid chromatographic column. Suitable mobile phases for use in the instant invention comprise any of those phases well known to those skilled in the art which will achieve a separation sufficient to enable a satisfactory quantitative analysis of the nitrated compounds present in the sample. A typical mobile phase for use in the instant analysis method comprises mixtures of lower aliphatic alcohols, such as, for example, methanol, with water. However, it is to be emphasized that the particular mobile phase employed in the instant analysis method is not critical, and that the instant invention contemplates that any mobile phase which achieves an efficient separation of the nitro compounds may be utilized herein.

After separating the nitrated compounds, such as the explosives RDX, HMX, TNT, and the degradation products thereof on the liquid chromatographic column, the absorbance of the eluant in the ultraviolet region is monitored. The UV absorbance of the eluant may be monitored at any suitable wavelength within the ultra-violet region. However, as the nitro-group of the nitrated compounds absorbs strongest at 230 nanometers (nm), in a preferred embodiment, the absorbance of the eluant is monitored at this wavelength.

The analysis method of the instant invention may be successfully utilized in the analysis of any type of liquid sample, and as has been emphasized supra, due to its high sensitivity is particularly advantageous for use in the environmental analysis of waste water for nitrated compounds, and particularly for the nitrated explosives, such as HMX, RDX, TNT, and the degradation products thereof. Determination of these compounds in non-liquid samples, such as, for example, soil, can also easily be achieved by extracting the nitrated compounds therefrom with a suitable solvent. In the analysis of waste water samples, applicants have found that best results are obtained by filtering the waste water sample, and then washing the resultant filtrate with a suitable solvent, such as, for example, tetrahydrofuran, to recover any nitrated compounds which may have been adsorbed on any suspended matter present therein prior to chromatographic analysis of the sample. Through the use of this filtration and THF wash step, not only is the accuracy of the analysis greatly enhanced, but column life is greatly extended. Experiments with labeled samples have shown that the filtration and THF wash step is sufficient to recover approximately all of the nitrated compounds adsorbed on the suspended matter present in waste water samples.

In order to more fully describe the present invention, the following examples are presented which are intended to be merely illustrative and not in any sense limitative of the invention.

EXAMPLE 1

100 microliters of a standard solution of 10 ppm each of HMX, RDX, and TNT was analyzed by the analysis method of the instant invention at ambient temperature. A reverse-phase, high performance liquid chromatographic column (30 centimeters by 4.6 millimeters internal diameter, $\mu$ Bondapak $C_{18}$, Waters Associates) was utilized for the separation. The mobile phase (40% methanol and water) was delivered by a high pressure pump (Varian Corporation, Model 4100), and the column eluant was monitored at 230 nm with a variable-wavelength UV detector (Dupont Corporation, Model 837). Injections were made via a large-volume sample loop (Rheodyne Corporation, Model 7105), and an automatic digital integrator (Infotronics Corporation, Model CRS-204) was used for quantification. The mobile-phase flow rate was maintained at 100 milliliters per hour, resulting in a column pressure drop of about 2500 psi at room temperature. Distilled-in-glass grade methanol and distilled water were used as the mobile-phase solvent. Meta-nitrophenol was used as the internal standard. The chromatogram illustrating this analysis is shown in FIG. 1. As can be seen therein, the analysis method of the instant invention achieves a highly efficient separation of each of these explosives. The identity of each of the explosive peaks was confirmed by mass spectroscopy.

EXAMPLE 2

Figure 2:
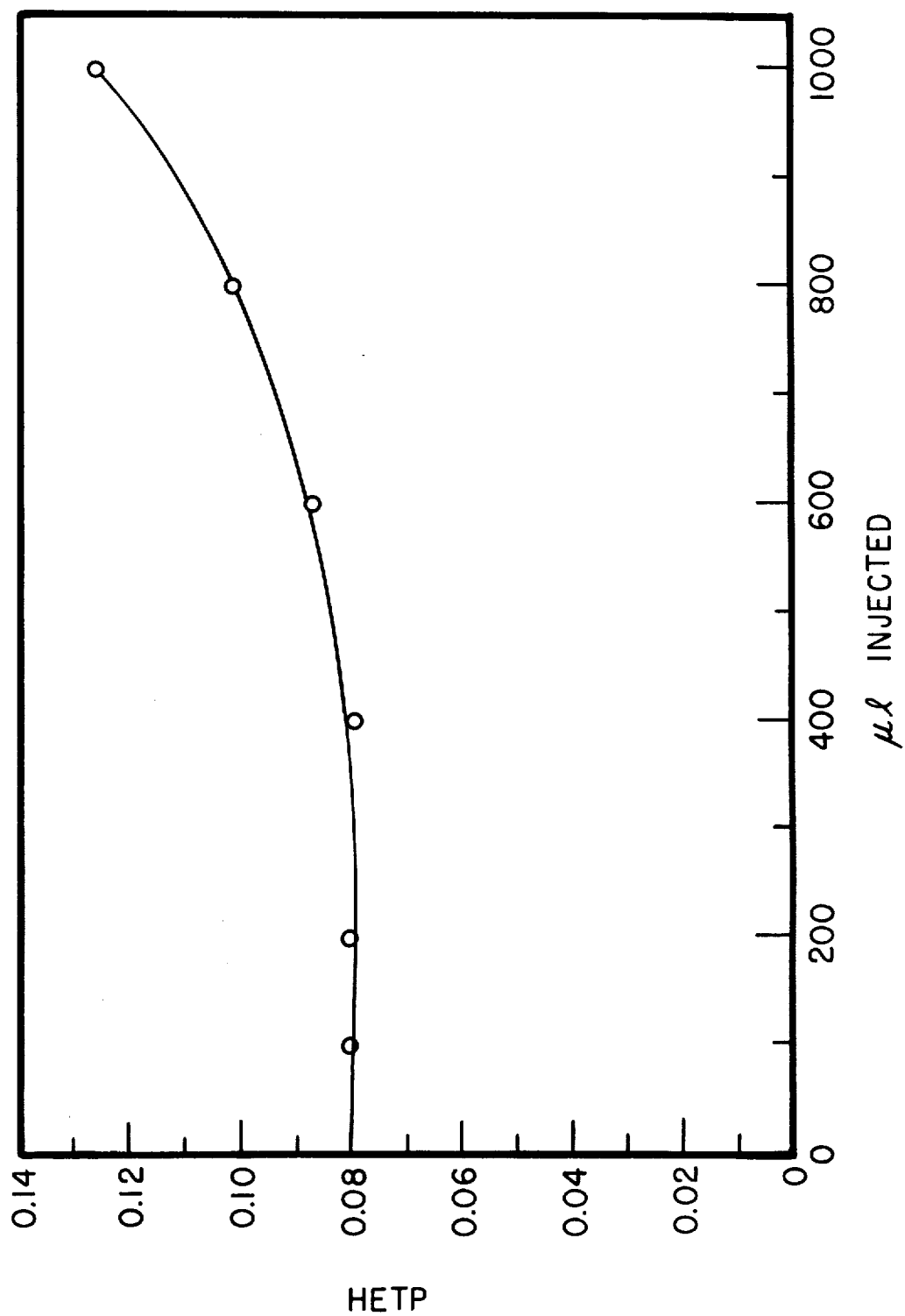
FIG. 2 is a graph illustrating the effect of injection volume on chromatographic efficiency for the compounds HMX, RDX, and TNT.

In order to determine the effect of injection volume on the chromatographic efficiency of the instant analysis method, the experiment of Example 1 was repeated using a plurality of different sized samples. The chromatographic conditions were identical with those of Experiment 1 with the exception that a flow velocity of 0.22 cm/sec. was employed. FIG. 2 represents a plot of chromatographic efficiency versus injection volume for each sample analyzed. As seen in FIG. 2, up to about 400 microliters of sample solution can be injected in the analysis method of the instant invention with no significant loss in resolution or change in retention time.

EXAMPLE 3

Figure 3:
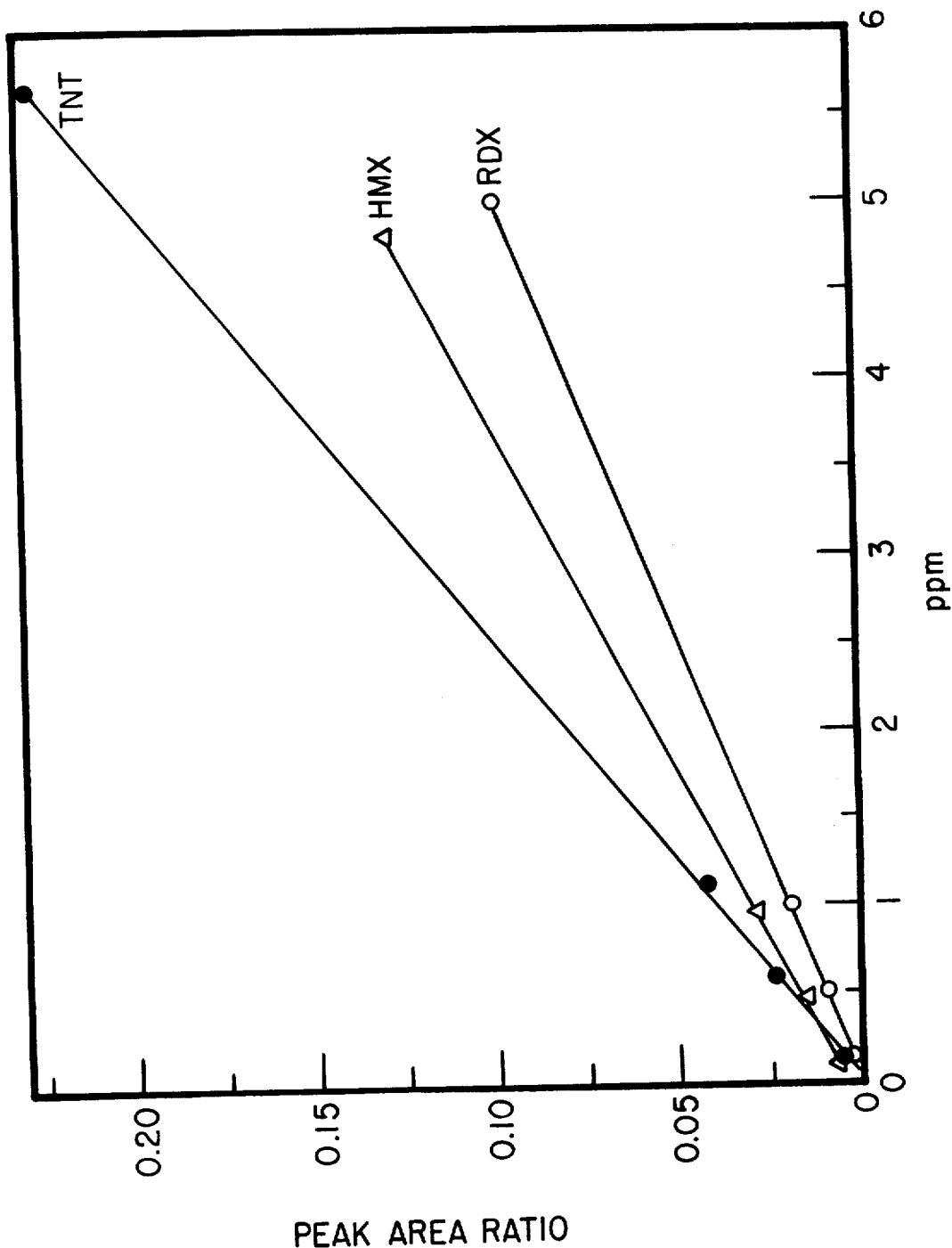
FIG. 3 is a graph illustrating standard curves correlating peak area ratio with concentration for the compounds HMX, RDX, and TNT.

A standard curve relating concentration of the compounds HMX, RDX, and TNT to peak ratio area, shown in FIG. 3, was prepared by injecting 100 microliter samples containing varying amounts of the aforementioned nitrated explosives, and 5 micrograms of meta-nitrophenol as internal standard (IS) into the apparatus and under the conditions described in Example 1. As an additional check on the reproducibility of the present analysis method, a plurality of different concentration TNT samples were prepared, and a number of analyses were conducted for each concentration. After analysis, the percent relative standard deviation for each TNT concentration was measured, the results of which are set forth in the accompanying Table.

TABLE

| REPRODUCTIBILITY OF INJECTION OF TNT | | |
| --- | --- | --- |
| Concentration (ppm) | No. of injections | % Relative standard deviation |
| 11.20 | 5 | 2.62 |
| 5.70 | 5 | 1.95 |
| 1.12 | 5 | 1.95 |
| 0.57 | 5 | 2.46 |
| 0.11 | 5 | 4.08 |

As seen in FIG. 3 and the above Table, the ratio of peak areas to internal standard was linear from about 100 ppb to 5 ppm, and satisfactory reproducibilities were obtained with samples having a cocentration as low as 100 ppb.

EXAMPLE 4

Figure 4:
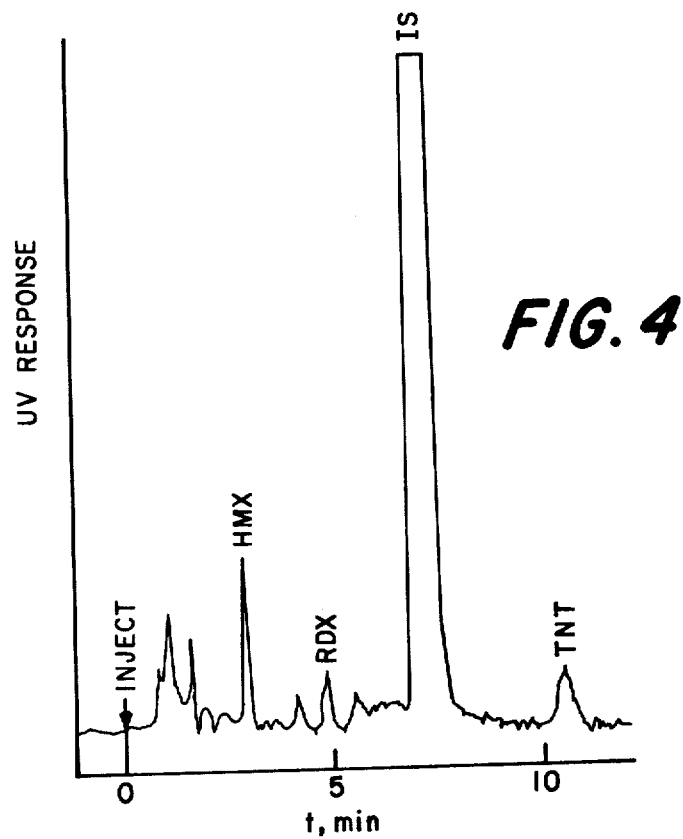
FIG. 4 is a chromatogram identical to FIG. 1 obtained by analyzing a 200 microliter sample of a standard solution containing 25 ppb each of HMX, RDX, and TNT, according to the analysis method of the instant invention.

200 microliters of a sample containing 25 parts per billion of each of the explosives HMX, RDX, and TNT was analyzed by the analysis method of the instant invention under the conditions described in Example 1. The results of this analysis are shown in FIG. 4. As seen therein, even at such extremely low concentrations, a good separation of each explosive was obtained.

EXAMPLE 5

Figure 5:
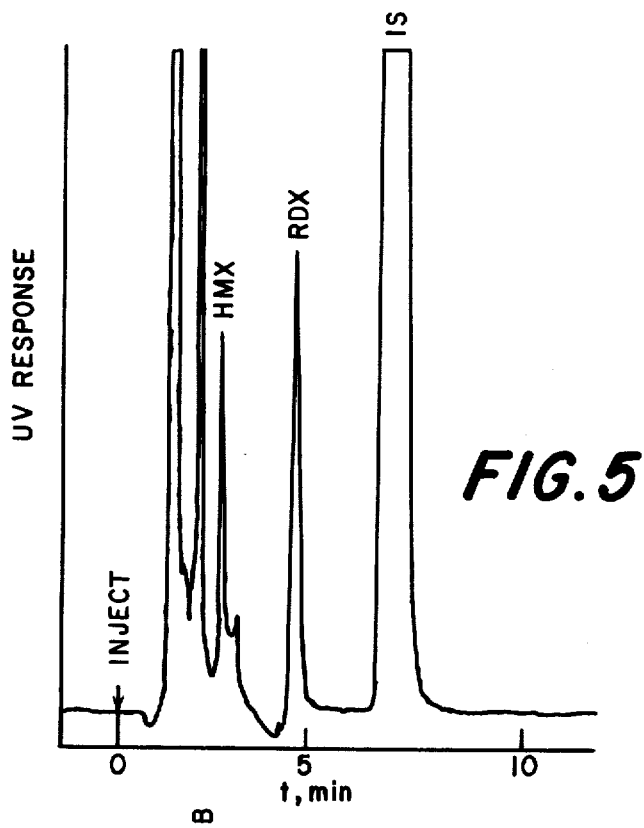
FIG. 5 is a chromatogram illustrating a typical analysis of a waste water sample by the analysis method of the instant invention; and, FIG. 6 is a chromatogram illustrating the use of the analysis method of the instant invention for detecting other types of nitrated compounds, specifically, TNT and its degradation products in a liquid sample.

A waste water sample obtained from a munitions production site was examined using the high performance liquid chromatography method of the instant invention. A 10 milliliter sample was first filtered through a teflon filter (Millipore, FGLPO1300) which had first been moistened with tetrahydrofuran. The filter was then washed with 1 milliliter of THF, and the THF wash was added to the filtered water in order to recover any explosives which may have remained adsorbed on the filtrate. 50 micrograms of meta-nitrophenol as internal standard (IS) were added per milliliter of filtered water, and 100 microliters of the filtered waste water sample was analyzed under the conditions of Example 1. FIG. 5 illustrates an analysis of this typical waste water sample. While a considerable amount of non-explosive UV absorbing compounds were present with the nitro-explosives, these compounds did not interfere with the analysis since their retention times on the column were shorter than those of the munitions analyzed. As shown in FIG. 5, each of the explosives were cleanly separated and with a high resolution. The identity of the explosives' peaks were confirmed by mass spectroscopy.

EXAMPLE 6

Figure 6:
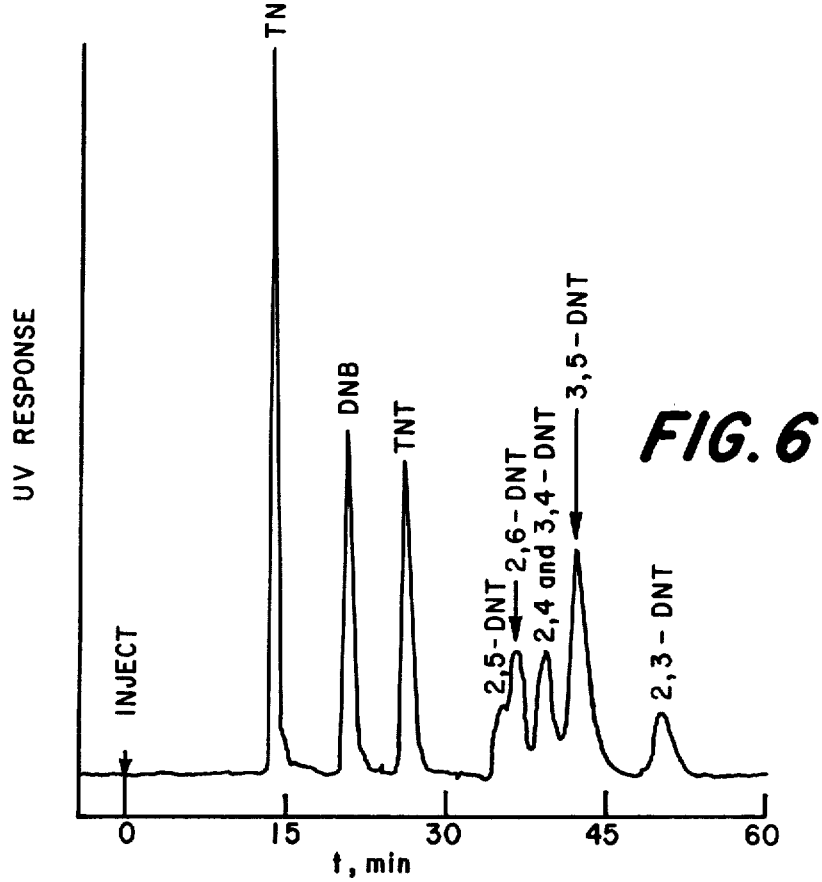

In order to demonstrate the suitability of the instant invention for use in the quantitative analysis of other types of compounds, a 100 microliter sample of TNT and its various degradation product was analyzed by the analysis method of the instant invention under the conditions described in Example 1. In order to enhance separation, however, two columns connected in series were employed. As shown in FIG. 6, the TNT degradation products were efficiently separated with a high degree of resolution.

The foregoing examples clearly demonstrate the suitability for the analysis method of the instant invention for the detection of nitrated compounds, and particularly the nitro-amine and nitroaromatic explosives HMX, RDX, TNT, and the degradation products thereof. As can be seen from these examples, by directly injecting the liquid sample containing these compounds onto a high performance liquid chromatographic column, not only are handling losses minimized, but the large sample volume which can be readily accommodated by this type of chromatography enable trace quantities of nitrated compounds to be rapidly and accurately quantitatively determined. Accordingly, the method of the instant invention provides a much needed contribution to the quantitative analysis art.

While the invention has now been described in terms of certain preferred embodiments, and illustrated by numerous examples, the skilled artisan will readily appreciate that various modifications, substitutions, omissions, and changes may be made without departing from the spirit thereof. Accordingly, it is intended that the scope of the present invention be limited solely by the scope of the following claims.

What is claimed is:

1. A method for the quantitative detection of aliphatic nitro-amine and nitroaromatic munitions selected from the group consisting of 1,3,5,7-tetranitro-1,3,5,7-tetraazacyclooctane, 1,3,5-trinitro-1,3,5-triazacyclohexane, 2,4,6-trinitrotoluene, combinations thereof, and the degradation products thereof, in liquid samples, comprising the steps of:

(a) directly injecting up to 400 microliters of a non-concentrated liquid sample containing said munitions in trace amounts as low as 25 parts per billion onto a reverse phase, high performance liquid chromatographic column;

(b) chromatographically separating said munitions on said column by elution with a mobile phase comprising methanol and water; and, (c) monitoring the absorbance of the resulting eluant in the ultra-violet region to provide a quantitative determination of the munitions present in said sample.

2. The process of claim 1, wherein said eluant is monitored at about 230 nm wavelength.

3. The process of claim 1, wherein said mobile phase comprises approximately 40% methanol in water.

4. The process of claim 1, wherein a plurality of chromatographic columns connected in series is utilized for separating said munitions.

5. The process of claim 1, wherein said liquid sample comprises a sample of waste water.

6. The process of claim 5, further comprising the steps of filtering said liquid sample on a tetrahydrofuran moistened filter to produce a filtrate and a liquid filtrant containing said munitions, and washing said filtrate with tetrahydrofuran to recover any of said munitions remaining on said filtrate.

* * * * *